US00PP11624P

United States Patent [19]

Henny

[11] Patent Number: Plant 11,624

[45] Date of Patent: Nov. 7, 2000

[54] MANDEVILLA PLANT NAMED 'BEST RED'

[75] Inventor: Richard J. Henny, Tavares, Fla.

[73] Assignee: Gem Ornamentals, Inc., Tavares, Fla.

[21] Appl. No.: 09/174,612

[22] Filed: Oct. 19, 1998

[51] Int. Cl.[7] ..... A01H 5/00

[52] U.S. Cl. ..... Plt./232

[58] Field of Search ..... Plt./232

*Primary Examiner*—Howard J. Locker
*Assistant Examiner*—Michelle Kizilkaya

[57] ABSTRACT

A new variety of a *Mandevilla* plant is characterized by bright red funnelform to trumpet-shaped bright red flowers with slightly diamond-shaped corolla lobes opening deep pink and darkening to red within one to two days after anthesis and remaining on the plant an additional three to four days, and elliptical, ovate-shaped, leathery, dark green and evergreen leaves.

1 Drawing Sheet

BACKGROUND OF THE INVENTION

The present invention relates to a new and distinct hybrid of Mandevilla that originated from self-pollination of Mandevilla×'Alice du Pont' (unpatented). Mandevilla×'Alice du Pont' is a hybrid from a cross of [*M. splendens*× (unknown species)]×*M. splendens* according to Bailey (see references). Pollinations were made by the inventor in a greenhouse at Gem Ornamentals Inc. in Tavares, Fla., in 1995. The new variety is a tender perennial that will freeze at temperatures of 32° F. or below. This new variety was selected for further evaluation because it had bright red flower color and large flower size. The new variety has been reproduced by asexual propagation (cuttings) near Tavares, Fla. Each of the progeny exhibits identical characteristics to the original plant establishing this hybrid as reproducible and true to type.

This new variety is unlike any Mandevilla commercially available nor like those described by Graf or Bailey (see references) as evidenced by the following unique combinations of characteristics:

1. Bright red flowers -large funnelform to trumpet-shaped bright red flowers with slightly diamond-shaped corolla lobes, opening deep pink and darkening to red within 1–2 days after anthesis and remaining on the plant an additional 3–4 days. White blotchy pattern irregular but occurring on all corolla lobes.

2. Elliptical -ovate shaped, leathery, dark green and evergreen leaves, measuring 7.7 to 12.0 cm. in length and 4.2 to 5.7 cm. in width.

BOTANICAL DESCRIPTION

Figure 1:
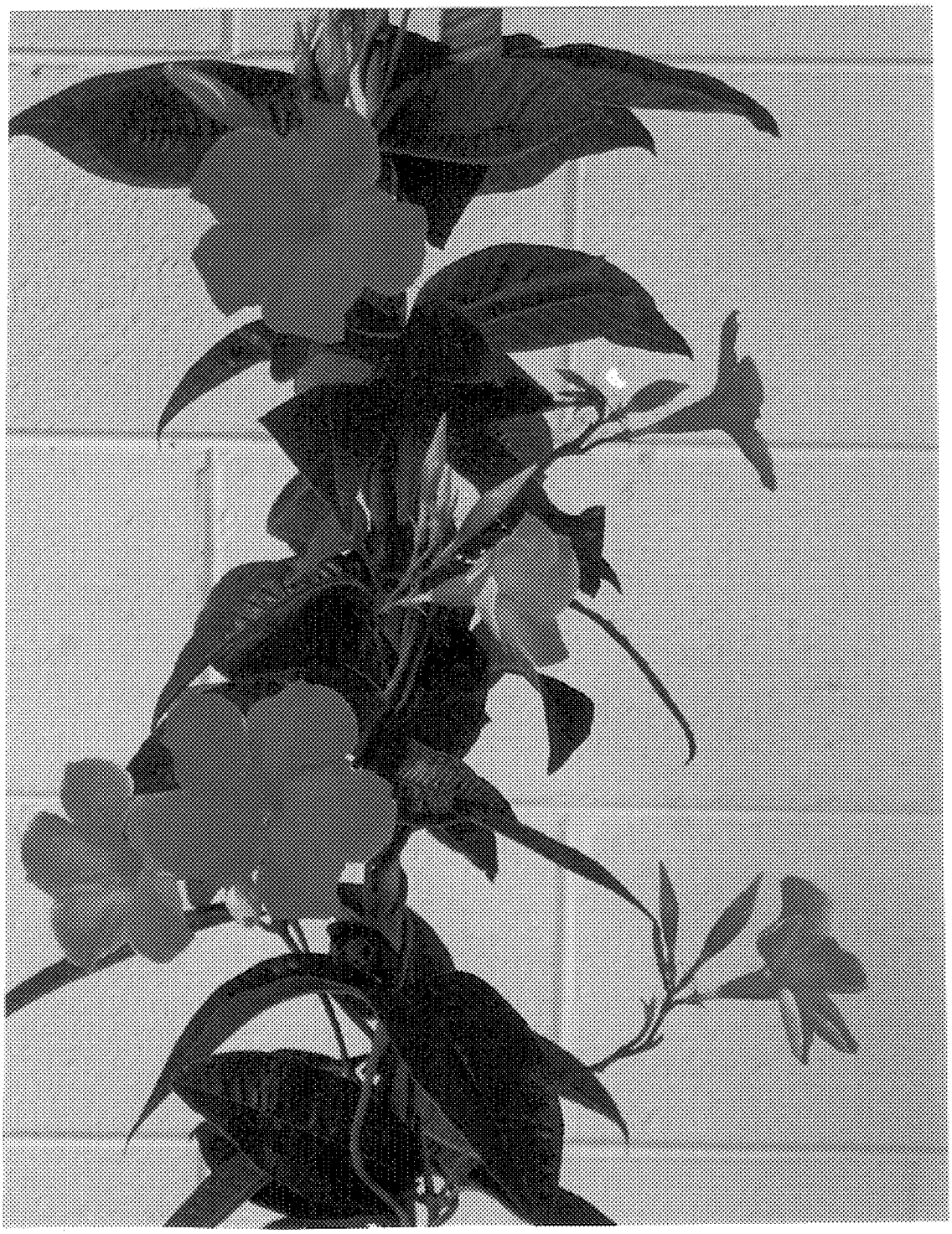
FIG. 1 is a photographic print in full color of a section of a two year old plant illustrating the mature red flowers, shiny leaves, and vining growth habit.

The following is a detailed description of the new Mandevilla plant based on observations in Tavares, Fla., where cuttings were rooted. The color determinations and comparisons are all based on The Royal Horticultural Society (R.H.S.) Colour Chart.

Overall size and growth habit:

*Size.*—The ultimate size of the new variety is unknown as no plant has reached full maturity. This new hybrid has grown between 1 to 1.5 m. in 2 months under greenhouse conditions in the summer in Tavares, Fla. The maximum size observed has been a plant with several vines reaching 3.5 to 4.0 meters during one growth season (April through October) in Tavares, Fla. Ultimate size will be determined by environment, length of growing season and cultural practices such as light and nutritional levels.

*Growth habit.*—The growth habit is a vining liana, twisting counter-clockwise with opposite evergreen, elliptic to obovate leaves and large funnelform to trumpet-shaped bright red flowers borne in axillary clusters on new growth.

Stems. The stems are olive-green, R.H.S. Colour Chart Fan 3, Yellow-Green Group No. 144B; lighter towards the tips, R.H.S. Colour Chart Fan 3, Yellow-Green Group No. 144C. Stems are often tinged R.H.S. Colour Chart Fan 2, Red Purple Group 59B. Stems densely velvety, tomentose, hairs erect and colorless as seen with the naked eye.

Foliage:

*Type.*—Evergreen, herbaceous.
*Arrangement.*—Opposite.
*Shape.*—Elliptic to obovate.
*Length.*—7.7 to 12.0 cm.
*Width.*—4.2 to 5.7 cm.
*Apex.*—Acuminate.
*Base.*—Cordate.
*Margin.*—Entire.
*Texture.*—Leathery, minutely hairy.
*Petiole.*—0.5 to 1.0 cm.
*Venation.*—Pinnate.
*Color.*—Upper side of a mature leaf is glittering R.H.S. Colour Chart Fan 3, Green Group 147A, midrib and veins are R.H.S. Colour Chart Fan 3, Green Group 143C. Under side of a mature leaf is opaque R.H.S. Colour Chart Fan 3, 146A.

Inflorescence:

*Type.*—Simple raceme, apparently indeterminate.
*Position.*—Lateral, axillary, one per node.
*Peduncle.*—5.7 to 8.4 cm. (axil to first bud scar).
*Raceme length.*—9.5 to 21.5 cm. (base to highest bud).
*Number of buds.*—3 to 5.
*Size of flower buds.*—8 to 10 cm. before opening.
*Number of open blooms.*—1 to 2.
*Pedicel.*—Twisted, 1.7 to 2.1 cm.
*Bracts.*—Herbaceous, triangular, apex acute, 0.50 to 0.90 cm. long, 0.30 to 0.55 cm. wide.
*Sepals.*—1.0 to 1.2 cm in length; 5 sepals per flower.
*Corolla tube.*—Straight; glabrous outside. Length 1.5 to 1.8 cm. Diameter at base 0.3 cm.
*Corolla throat.*—Conical. Length 3.5 to 3.8 cm. Opening width 2.0 to 2.2 cm.

*Corolla width.*—10.0 to 12.0 cm.

*Corolla lobes.*—Unequally sided and diamond-shaped, apex obtuse, slightly eccentric, broadly spatulate to obovate, margins minutely undulate, subentire, glabrous. Length 4.5 to 5.5 cm.; width 3.7 to 5.0 cm.

*Color.*—Bud: rachis: R.H.S. Colour Chart Fan 3, Yellow-Green Group 144C. pedicel: On bud and newly opening flower, R.H.S. Colour Chart Fan 3, Yellow Green Group 144 C bractiole: R.H.S. Colour Chart Fan 3, Yellow-Green Group 144C. New Bloom: Outside: sepals:R.H.S. Colour Chart Fan 3, Yellow-Green Group 144C. Tips, margins and upper half are R.H.S. Colour Chart Fan 1, Red-Purple Group 60A. pedicels: R.H.S. Colour Chart Fan 2, Red-Purple Group 60A. corollatube: The basal 3–4 mm are R.H.S. Colour Chart Fan 3, Yellow-Green Group 144C. The upper portion of the tube is R.H.S. Colour Chart Fan 1, Red Group 53D. corolla throat: R.H.S. Colour Chart Fan 1, Red Group 53D. corolla lobes: R.H.S. Colour Chart Fan 1, Red Group 55C. Inside: corolla lobes: R.H.S. Colour Chart Fan 1, Red Group 65C. Midline area between the narrow and wider lobe halves is R.H.S. Colour Chart Fan 1, Red Group 55A. The lower ⅓ of the throat is R.H.S. Colour Chart Fan 3, Yellow-Green Group 145D. The rest of the throat is R.H.S. Colour Chart Fan 1, Red Group 55 B. At the top of the throat at the junction of the lobe proper is a narrow, irregular border of R.H.S. Colour Chart Fan 1, Red Group 55A. The apex darkens to R.H.S. Colour Chart Fan 1, Red Group 54A. Old Bloom (2 days after anthesis) Outside: corolla tube: The lower one-third of the corolla tube is R.H.S. Colour Chart Fan 4, White 155A. The remainder of the corolla tube is R.H.S. Colour Chart Fan 1, Red Group 53C. corolla lobes: The color throughout is R.H.S. Colour Chart Fan 1, Red Group 53C. Inside: corolla lobe and tube: The color throughout is R.H.S. Colour Chart Fan 1, Red Group 53C.

*Tubers.*—The tubers taken from a one year old plant were irregular in shape varying from cylindrical to globose with constrictions occurring at regular intervals. The diameter was between 0.5 cm. and 2.0 cm. Their color was R.H.S. Colour Chart Fan 4, Grey-Brown Group 199A.

*Fruit and seed.*—No fruit or seed have been observed on the new variety. However, anthers produce pollen and are normal in appearance.

*Bloom fragrance.*—Flowers are faintly fragrant in the late afternoon but not distinguishable from the parent plant.

*Blooming season.*—Under normal central Florida conditions the new variety will flower from early April through the end of October. Flowers last 4–6 days which is similar to other varieties.

*Disease resistance.*—The new variety has disease resistance similar to other varieties. No unusual disease resistance has been noted in the new variety.

*Cold hardiness.*—The new variety has withstood temperatures of 34° F. but is not frost tolerant.

DISTINGUISHING DATA

Mandevilla×'Alice du Pont' The new variety is distinguishable from Mandevilla×'Alice du Pont' in the following respects:

Mandevilla×'Alice du Pont':

*Leaf shape.*—elliptic-oblong to ovate-oblong.

*Leaf length.*—10 cm. to 13 cm., longer than the new variety.

*Leaf width.*—4 cm. to 6.5 cm., slightly wider than the new variety.

*Petiole length.*—0.4 cm. to 0.7 cm., shorter than the new variety.

*Flower color.*—'Alice du Pont' corolla opens pink, R.H.S. Colour Chart Fan 2, Red-Purple Group 63C, but darkens to R.H.S. Colour Chart Fan 2, Red Purple Group 63A.The new variety opens in the red group, R.H.S. Colour Chart Fan 1, Red Group 55C and darkens in the red group to 55B two days after anthesis.

Throat color of 'Alice du Pont' opens striated dark pink R.H.S. Colour Chart Fan 2, Red-Purple Group 64C and darkens to 63A. The new variety's throat opens R.H.S. Colour Chart Fan 1, Red Group 53D and darkens to 53C. White, R.H.S. Colour Chart Fan 4. White Group 155B is also visible at the base of the throat around the stamens of a mature flower of 'Alice du Pont'. The new variety's throat is yellow -green as previously described. The overall growth habit of the new variety is similar to the parent variety 'Alice du Pont'. Mandevilla 'Ruby Star' The new variety is distinguishable from Mandevilla 'Ruby Star' (U.S. Plant Pat. No. 8,842) in the following respects:

Mandevilla 'Ruby Star':

*Leaf shape.*—oblong to elliptic.

*Leaf length.*—13 .3 to 15.5 cm., longer than the new variety.

*Leaf width.*—4.0 to 5.3 cm. narrower than the new variety.

*Margin.*—repand and revolute.

*Corolla lobes.*—Irregularly obovate, apexes off-centered, 5.0 to 5.4 cm. length by 3.5 to 4.0 cm. width.

*Flower color.*—The color of the outside of the corolla tube of Mandevilla 'Ruby Star' 2 days after anthesis is R.H.S. Colour Chart Fan 1, Red Group 53A. 'Best Red' is R.H.S. Colour Chart Fan 1, Red Group 53 C throughout. The corolla throat and the narrow portion of the corolla lobe of Mandevilla 'Ruby Star' are R.H.S. Colour Chart Fan 1, Red Group 46A. The wider side of the corolla lobe is R.H.S. Colour Chart Fan 1, Red Group 53C along the midrib. 'Best Red' is R.H.S. Colour Chart Fan 1, Red Group 53C throughout.

The color throughout the inside corolla lobe of Mandevilla 'Ruby Star' is R.H.S. Colour Chart Fan 1, Red Group 46B. This color extends approximately 1 cm. into the upper portion of the throat. The Color is most prominent along the veins. Between the veins the Color lightens to R.H.S. Colour Chart Fan 2, Red-Purple Group 63B. This results in a striping effect. The five bands along the fusion line of the petals is now R.H.S. Colour Chart Fan 4, White Group 155A and extend all the way to the base of the throat. The yellow bands now extend only about ¼ of the way up the throat and are now R.H.S. Colour Chart Fan 3, Yellow-Green Group 150D. The lobe and throat of Mandevilla 'Best Red' are R.H.S. Colour Chart Fan 1, Red Group 53C throughout.

REFERENCES

Bailey, L.H. and Bailey, E.Z., Hortus Third, Macmillian, New York (1976), p. 711.

Graf, A. B. Tropica — Color Cyclopedia of Exotic Plants and Trees, Roehrs Co., East Rutherford, New Jersey (1978) P. 1030.

U.S. Plant Pat. No. 8,842 Jul. 19, 1994, Mandevilla: "Ruby Star", Richard J. Henny.

I claim:

1. A new and distinct variety of Mandevilla plant substantially shown and described, characterized by bright red flowers.

* * * * *